(12) United States Patent
Lee et al.

(10) Patent No.: US 11,478,925 B2
(45) Date of Patent: Oct. 25, 2022

(54) ROBOT AND METHOD FOR CONTROLLING SAME

(71) Applicant: LG ELECTRONICS INC., Seoul (KR)

(72) Inventors: Joonwon Lee, Seoul (KR); Reaok Ko, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 373 days.

(21) Appl. No.: 16/737,610

(22) Filed: Jan. 8, 2020

(65) Prior Publication Data

US 2021/0053213 A1  Feb. 25, 2021

(30) Foreign Application Priority Data

Aug. 23, 2019  (KR) .................. 10-2019-0103470

(51) Int. Cl.
| | |
|---|---|
| *B25J 9/16* | (2006.01) |
| *G06N 3/00* | (2006.01) |
| *B25J 11/00* | (2006.01) |
| *G06N 3/08* | (2006.01) |
| *G06N 3/04* | (2006.01) |

(52) U.S. Cl.
CPC ........... *B25J 9/163* (2013.01); *B25J 11/0005* (2013.01); *G06N 3/008* (2013.01); *G06N 3/04* (2013.01); *G06N 3/08* (2013.01)

(58) Field of Classification Search
USPC .................................................. 700/245–264
See application file for complete search history.

(56) References Cited

U.S. PATENT DOCUMENTS

| | | | | |
|---|---|---|---|---|
| 6,895,305 | B2 * | 5/2005 | Lathan | G16H 20/30 600/101 |
| 8,830,057 | B1 * | 9/2014 | Poursohi | G01N 33/00 700/245 |
| 9,552,056 | B1 * | 1/2017 | Barry | B25J 9/1689 |
| 10,762,414 | B1 * | 9/2020 | Marggraff | G06N 3/008 |
| 2012/0185094 | A1 * | 7/2012 | Rosenstein | G05D 1/0272 901/1 |
| 2014/0254896 | A1 * | 9/2014 | Zhou | G06Q 20/40145 705/16 |
| 2018/0366121 | A1 * | 12/2018 | Funazukuri | G10L 15/22 |
| 2019/0366557 | A1 * | 12/2019 | Gewickey | G06N 5/046 |
| 2019/0366558 | A1 * | 12/2019 | Gupta | B25J 11/0005 |
| 2020/0036810 | A1 * | 1/2020 | Howard | G06F 16/5854 |
| 2021/0001077 | A1 * | 1/2021 | Stevens | B25J 13/003 |

FOREIGN PATENT DOCUMENTS

WO  WO-2020215085 A1 * 10/2020 ............ A61M 21/00

\* cited by examiner

*Primary Examiner* — Jonathan L Sample
(74) *Attorney, Agent, or Firm* — Birch, Stewart, Kolasch & Birch, LLP

(57) ABSTRACT

A robot according to an embodiment of the present disclosure includes a body which is provided with a battery therein, a head connected to a front or an upper side of the body, a mouth formed on one side of the head and include a fixed portion and a rotatable portion disposed below the fixed portion, a mouth driver configured to rotate the rotatable portion in a vertical direction, a biometric information sensor disposed inside the mouth and exposed to the outside during the lower rotation of the rotatable portion, and a processor configured to acquire health state information of a user through the biometric information sensor.

18 Claims, 11 Drawing Sheets

ROBOT AND METHOD FOR CONTROLLING SAME

CROSS-REFERENCE TO RELATED APPLICATIONS

The present application claims priority under 35 U.S.C. 119 and 35 U.S.C. 365 to Korean Patent Application No. 10-2019-0103470 (filed on Aug. 23, 2019), which is hereby incorporated by reference in its entirety.

BACKGROUND

The present disclosure relates to a robot, and more particularly, to a robot capable of monitoring the health state of a user and thus promoting effective health care, and a method for controlling the same.

To be in charge of a part of factory automation, robots have been developed for industrial use. Recently, as the robot applied field has been further expanded, medical robots and aerospace robots, as well as robots that can be used in daily life are being developed.

In particular, pet robots which mimic the appearance of pets such as dogs can provide emotional satisfaction to users. Such a pet robot can operate similar to a real pet and output a sound. Since the pet robots do not need to feed or the dung of the pet robots do not need to be put away, busy modern people can feel the same emotional satisfaction as a real pet while inconvenience and burden can be reduced, through the pet robot.

SUMMARY

An object to be solved by the present disclosure is to provide a robot which can monitor a health state of a user to assist the health care of the user.

Another object to be solved by the present disclosure is to provide a robot which can more stably acquire biometric information of the user.

A robot according to an embodiment of the present disclosure includes a body which is provided with a battery therein, a head connected to a front or an upper side of the body, a mouth formed on one side of the head and include a fixed portion and a rotatable portion disposed below the fixed portion, a mouth driver configured to rotate the rotatable portion in a vertical direction, a biometric information sensor disposed inside the mouth and exposed to the outside during the lower rotation of the rotatable portion, and a processor configured to acquire health state information of a user through the biometric information sensor.

According to an embodiment, the robot may further include a first proximity sensor provided in the head, in which the processor may be configured to control the mouth driver so as to rotate the rotatable portion downward by a predetermined angle in a case where the proximity of a part of a body of the user is detected through the first proximity sensor.

According to an embodiment, the processor may be configured to detect the contact of the part of the body of the user through the biometric information sensor, and control the mouth driver so as to rotate the rotatable portion upward.

According to an embodiment, the robot may further include a second proximity sensor provided on a lower side of the fixed portion, in which the processor may be configured to stop driving of the mouth driver in a case where a sensing value of the second proximity sensor is less than a reference value during upper rotation of the rotatable portion.

According to an embodiment, the processor may be configured to acquire a biometric signal of the user for a preset time through the biometric information sensor, acquire biometric information of the user based on the acquired biometric signal, and acquire health state information based on the acquired biometric information.

The biometric information may include at least one of heart rate, pulse characteristics, body temperature, stress, and oxygen saturation.

According to an embodiment, the processor may be configured to acquire the health state information corresponding to the acquired biometric information through a learning model trained based on machine learning so as to provide health state information from biometric information.

According to an embodiment, the robot may further include a communication interface configured to connect to a server, in which the processor may be configured to control the communication interface so as to transmit the biometric signal or the biometric information to the server, and receive the health state information corresponding to the biometric signal or the biometric information from the server.

According to an embodiment, the processor may be configured to control the mouth driver so as to rotate the rotatable portion downward after the biometric signal is acquired.

According to an embodiment, the processor may be configured to detect that the body of the user is separated by more than a reference distance through the first proximity sensor, and control the mouth driver so as to rotate the rotatable portion upward.

According to an embodiment, the processor may be configured to detect that the part of the body of the user is put into the mouth through the second proximity sensor, and control the mouth driver so as to rotate the rotatable portion upward.

According to an embodiment, the processor may be configured to set at least one of a walking cycle, a walking time, and a walking distance based on the health state information, control an output interface so as to output a message for inducing walking based on the set walking cycle, and control at least one driving motor based on at least one of a set time and a set distance.

A method for controlling a robot according to an embodiment of the present disclosure includes detecting proximity of a part of a body of a user, exposing a biometric information sensor to the outside if the proximity is detected, acquiring biometric information of the user as the body of the user is in contact with the biometric information sensor, acquiring health state information based on the acquired biometric information, and providing a health care assistance function based on the acquired health state information.

DETAILED DESCRIPTION OF THE EMBODIMENTS

Figure 1:
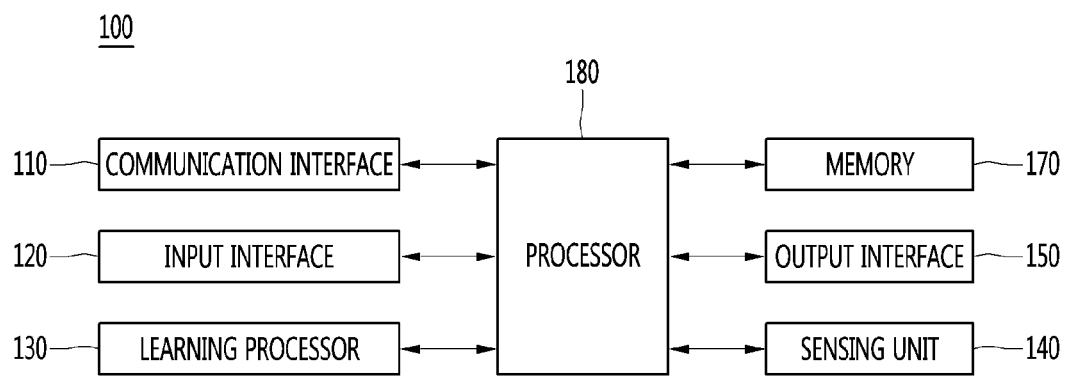
FIG. 1 is a view illustrating an AI device including a robot according to an embodiment of the present disclosure.

Hereinafter, an embodiment disclosed in the present specification will be described in detail with reference to the accompanying drawings. It should be understood that the accompanying drawings are only to facilitate understanding of the embodiment disclosed herein, but the technical spirit disclosed in the present specification is not limited by the accompanying drawings and includes all modifications, equivalents, and substitutes included in the spirit and technical scope of the present disclosure.

A robot may refer to a machine that automatically processes or operates a given task by its own ability. In particular, a robot having a function of recognizing an environment and performing a self-determination operation may be referred to as an intelligent robot.

Robots may be classified into industrial robots, medical robots, home robots, military robots, and the like according to the use purpose or field.

The robot includes a driving unit may include an actuator or a motor and may perform various physical operations such as moving a robot joint. In addition, a movable robot may include a wheel, a brake, a propeller, and the like in a driving unit, and may travel on the ground through the driving unit or fly in the air.

Artificial intelligence refers to the field of studying artificial intelligence or methodology for making artificial intelligence, and machine learning refers to the field of defining various issues dealt with in the field of artificial intelligence and studying methodology for solving the various issues. Machine learning is defined as an algorithm that enhances the performance of a certain task through a steady experience with the certain task.

An artificial neural network (ANN) is a model used in machine learning and may mean a whole model of problem-solving ability which is composed of artificial neurons (nodes) that form a network by synaptic connections. The artificial neural network can be defined by a connection pattern between neurons in different layers, a learning process for updating model parameters, and an activation function for generating an output value.

The artificial neural network may include an input layer, an output layer, and optionally one or more hidden layers. Each layer includes one or more neurons, and the artificial neural network may include a synapse that links neurons to neurons. In the artificial neural network, each neuron may output the function value of the activation function for input signals, weights, and deflections input through the synapse.

Model parameters refer to parameters determined through learning and include a weight value of synaptic connection and deflection of neurons. A hyperparameter means a parameter to be set in the machine learning algorithm before learning, and includes a learning rate, a repetition number, a mini batch size, and an initialization function.

The purpose of the learning of the artificial neural network may be to determine the model parameters that minimize a loss function. The loss function may be used as an index to determine optimal model parameters in the learning process of the artificial neural network.

Machine learning may be classified into supervised learning, unsupervised learning, and reinforcement learning according to a learning method.

The supervised learning may refer to a method of learning an artificial neural network in a state in which a label for learning data is given, and the label may mean the correct answer (or result value) that the artificial neural network must infer when the learning data is input to the artificial neural network. The unsupervised learning may refer to a method of learning an artificial neural network in a state in which a label for learning data is not given. The reinforcement learning may refer to a learning method in which an agent defined in a certain environment learns to select a behavior or a behavior sequence that maximizes cumulative compensation in each state.

Machine learning, which is implemented as a deep neural network (DNN) including a plurality of hidden layers among artificial neural networks, is also referred to as deep learning, and the deep learning is part of machine learning. In the following, machine learning is used to mean deep learning.

Self-driving refers to a technique of driving for oneself, and a self-driving vehicle refers to a vehicle that travels without an operation of a user or with a minimum operation of a user.

For example, the self-driving may include a technology for maintaining a lane while driving, a technology for automatically adjusting a speed, such as adaptive cruise control, a technique for automatically traveling along a predetermined route, and a technology for automatically setting and traveling a route when a destination is set.

The vehicle may include a vehicle having only an internal combustion engine, a hybrid vehicle having an internal combustion engine and an electric motor together, and an electric vehicle having only an electric motor, and may include not only an automobile but also a train, a motorcycle, and the like.

At this time, the self-driving vehicle may be regarded as a robot having a self-driving function.

FIG. 1 is a view illustrating an AI device including a robot according to an embodiment of the present disclosure.

The AI device 100 may be implemented by a stationary device or a mobile device, such as a TV, a projector, a mobile phone, a smartphone, a desktop computer, a notebook, a digital broadcasting terminal, a personal digital assistant (PDA), a portable multimedia player (PMP), a navigation device, a tablet PC, a wearable device, a set-top box (STB), a DMB receiver, a radio, a washing machine, a refrigerator, a desktop computer, a digital signage, a robot, a vehicle, and the like.

Referring to FIG. 1, the AI device 100 may include a communication interface 110, an input interface 120, a learning processor 130, a sensing unit 140, an output interface 150, a memory 170, and a processor 180.

The communication interface 110 may transmit and receive data to and from external devices such as other AI devices 100a to 100e and the AI server 200 by using wire/wireless communication technology. For example, the communication interface 110 may transmit and receive sensor information, a user input, a learning model, and a control signal to and from external devices.

The communication technology used by the communication interface 110 includes GSM (Global System for Mobile communication), CDMA (Code Division Multi Access), LTE (Long Term Evolution), 5G, WLAN (Wireless LAN), Wi-Fi (Wireless-Fidelity), Bluetooth™, RFID (Radio Frequency Identification), Infrared Data Association (IrDA), ZigBee, NFC (Near Field Communication), and the like.

The input interface 120 may acquire various kinds of data.

At this time, the input interface 120 may include a camera for inputting a video signal, a microphone for receiving an audio signal, and a user input interface for receiving information from a user. The camera or the microphone may be treated as a sensor, and the signal acquired from the camera or the microphone may be referred to as sensing data or sensor information.

The input interface 120 may acquire a learning data for model learning and an input data to be used when an output is acquired by using learning model. The input interface 120 may acquire raw input data. In this case, the processor 180 or the learning processor 130 may extract an input feature by preprocessing the input data.

The learning processor 130 may learn a model composed of an artificial neural network by using learning data. The learned artificial neural network may be referred to as a learning model. The learning model may be used to an infer result value for new input data rather than learning data, and the inferred value may be used as a basis for determination to perform a certain operation.

At this time, the learning processor 130 may perform AI processing together with the learning processor 240 of the AI server 200.

At this time, the learning processor 130 may include a memory integrated or implemented in the AI device 100. Alternatively, the learning processor 130 may be implemented by using the memory 170, an external memory directly connected to the AI device 100, or a memory held in an external device.

The sensing unit 140 may acquire at least one of internal information about the AI device 100, ambient environment information about the AI device 100, and user information by using various sensors.

Examples of the sensors included in the sensing unit 140 may include a proximity sensor, an illuminance sensor, an acceleration sensor, a magnetic sensor, a gyro sensor, an inertial sensor, an RGB sensor, an IR sensor, a fingerprint recognition sensor, an ultrasonic sensor, an optical sensor, a microphone, a lidar, and a radar.

The output interface 150 may generate an output related to a visual sense, an auditory sense, or a haptic sense.

At this time, the output interface 150 may include a display for outputting time information, a speaker for outputting auditory information, and a haptic module for outputting haptic information.

The memory 170 may store data that supports various functions of the AI device 100. For example, the memory 170 may store input data acquired by the input interface 120, learning data, a learning model, a learning history, and the like.

The processor 180 may determine at least one executable operation of the AI device 100 based on information determined or generated by using a data analysis algorithm or a machine learning algorithm. The processor 180 may control the components of the AI device 100 to execute the determined operation.

To this end, the processor 180 may request, search, receive, or utilize data of the learning processor 130 or the memory 170. The processor 180 may control the components of the AI device 100 to execute the predicted operation or the operation determined to be desirable among the at least one executable operation.

When the connection of an external device is required to perform the determined operation, the processor 180 may generate a control signal for controlling the external device and may transmit the generated control signal to the external device.

The processor 180 may acquire intention information for the user input and may determine the user's requirements based on the acquired intention information.

The processor 180 may acquire the intention information corresponding to the user input by using at least one of a speech to text (STT) engine for converting speech input into a text string or a natural language processing (NLP) engine for acquiring intention information of a natural language.

At least one of the STT engine or the NLP engine may be configured as an artificial neural network, at least part of which is learned according to the machine learning algorithm. At least one of the STT engine or the NLP engine may be learned by the learning processor 130, may be learned by the learning processor 240 of the AI server 200, or may be learned by their distributed processing.

The processor 180 may collect history information including the operation contents of the AI apparatus 100 or the user's feedback on the operation and may store the collected history information in the memory 170 or the learning processor 130 or transmit the collected history information to the external device such as the AI server 200. The collected history information may be used to update the learning model.

The processor 180 may control at least part of the components of AI device 100 so as to drive an application program stored in memory 170. Furthermore, the processor 180 may operate two or more of the components included in the AI device 100 in combination so as to drive the application program.

Figure 2:
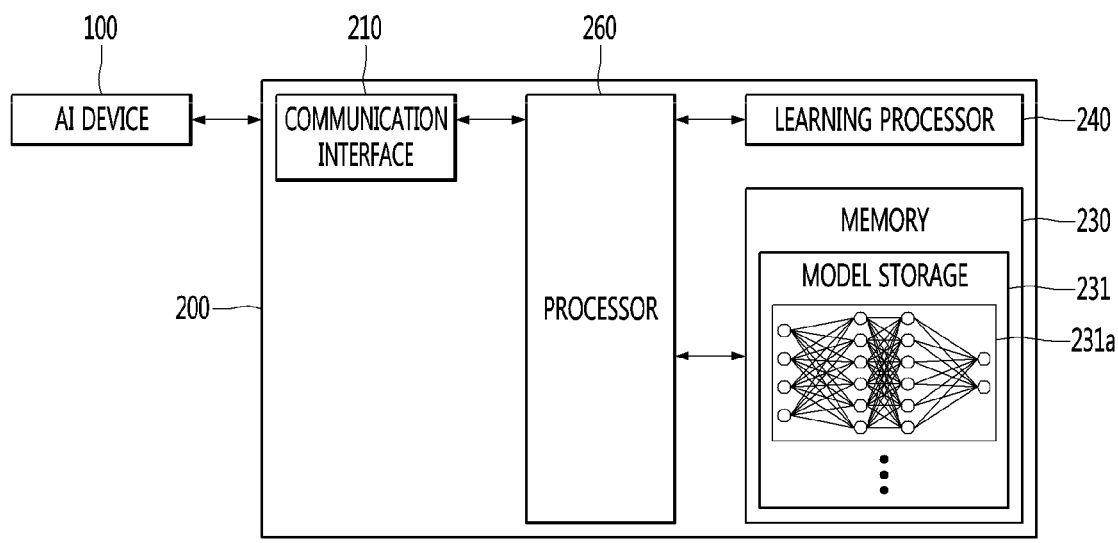
FIG. 2 is a view illustrating an AI server connected to a robot according to an embodiment of the present disclosure.

FIG. 2 is a view illustrating an AI server connected to a robot according to an embodiment of the present disclosure.

Referring to FIG. 2, the AI server 200 may refer to a device that learns an artificial neural network by using a machine learning algorithm or uses a learned artificial neural network. The AI server 200 may include a plurality of servers to perform distributed processing, or may be defined as a 5G network. At this time, the AI server 200 may be included as a partial configuration of the AI device 100, and may perform at least part of the AI processing together.

The AI server 200 may include a communication interface 210, a memory 230, a learning processor 240, a processor 260, and the like.

The communication interface 210 can transmit and receive data to and from an external device such as the AI device 100.

The memory 230 may include a model storage 231. The model storage 231 may store a learning or learned model (or an artificial neural network 231a) through the learning processor 240.

The learning processor 240 may learn the artificial neural network 231a by using the learning data. The learning model may be used in a state of being mounted on the AI server 200 of the artificial neural network, or may be used in a state of being mounted on an external device such as the AI device 100.

The learning model may be implemented in hardware, software, or a combination of hardware and software. If all or part of the learning models are implemented in software, one or more instructions that constitute the learning model may be stored in memory 230.

The processor 260 may infer the result value for new input data by using the learning model and may generate a response or a control command based on the inferred result value.

Figure 3:
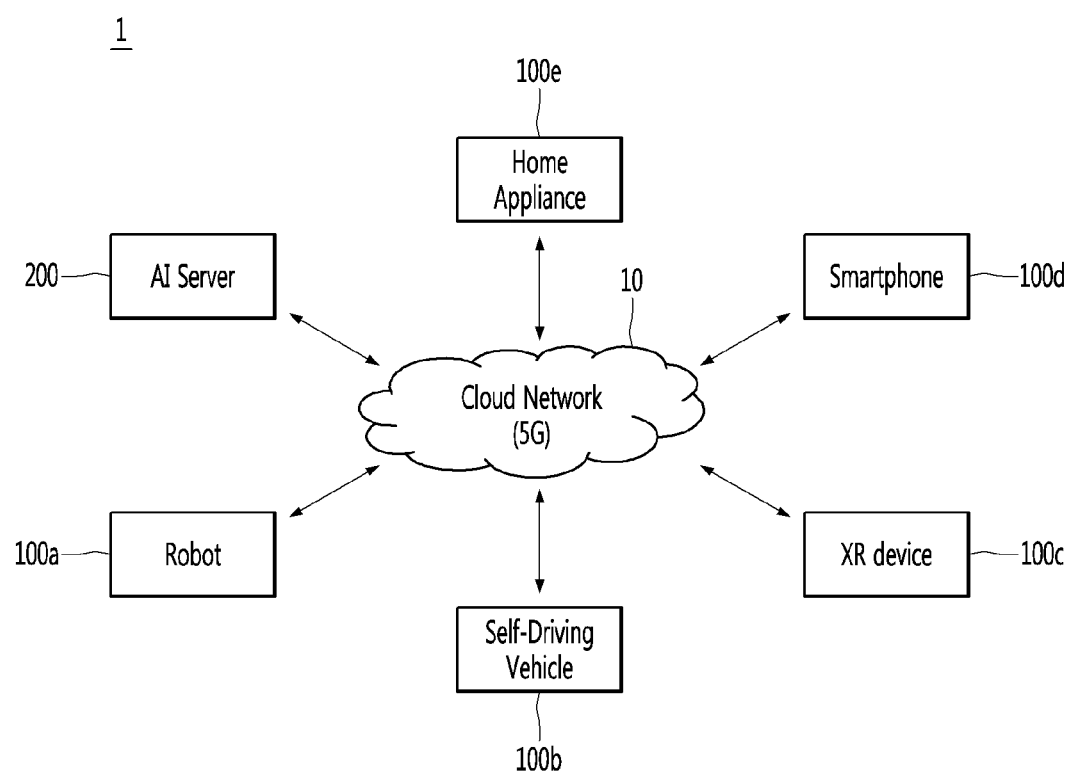
FIG. 3 is a view illustrating an AI system including a robot according to an embodiment of the present disclosure.

FIG. 3 is a view illustrating an AI system including a robot according to an embodiment of the present disclosure.

Referring to FIG. 3, in the AI system 1, at least one of an AI server 200, a robot 100a, a self-driving vehicle 100b, an XR device 100c, a smartphone 100d, or a home appliance 100e is connected to a cloud network 10. The robot 100a, the self-driving vehicle 100b, the XR device 100c, the smartphone 100d, or the home appliance 100e, to which the AI technology is applied, may be referred to as AI devices 100a to 100e.

The cloud network 10 may refer to a network that forms part of a cloud computing infrastructure or exists in a cloud computing infrastructure. The cloud network 10 may be configured by using a 3G network, a 4G or LTE network, or a 5G network.

That is, the devices 100a to 100e and 200 configuring the AI system 1 may be connected to each other through the cloud network 10. In particular, each of the devices 100a to 100e and 200 may communicate with each other through a base station, but may directly communicate with each other without using a base station.

The AI server 200 may include a server that performs AI processing and a server that performs operations on big data.

The AI server 200 may be connected to at least one of the AI devices constituting the AI system 1, that is, the robot 100a, the self-driving vehicle 100b, the XR device 100c, the smartphone 100d, or the home appliance 100e through the cloud network 10, and may assist at least part of AI processing of the connected AI devices 100a to 100e.

At this time, the AI server 200 may learn the artificial neural network according to the machine learning algorithm instead of the AI devices 100a to 100e, and may directly store the learning model or transmit the learning model to the AI devices 100a to 100e.

At this time, the AI server 200 may receive input data from the AI devices 100a to 100e, may infer the result value for the received input data by using the learning model, may generate a response or a control command based on the inferred result value, and may transmit the response or the control command to the AI devices 100a to 100e.

Alternatively, the AI devices 100a to 100e may infer the result value for the input data by directly using the learning model, and may generate the response or the control command based on the inference result.

Hereinafter, various embodiments of the AI devices 100a to 100e to which the above-described technology is applied will be described. The AI devices 100a to 100e illustrated in FIG. 3 may be regarded as a specific embodiment of the AI device 100 illustrated in FIG. 1.

The robot 100a, to which the AI technology is applied, may be implemented as a guide robot, a carrying robot, a cleaning robot, a wearable robot, an entertainment robot, a pet robot, an unmanned flying robot, or the like.

The robot 100a may include a robot control module for controlling the operation, and the robot control module may refer to a software module or a chip implementing the software module by hardware.

The robot 100a may acquire state information about the robot 100a by using sensor information acquired from various kinds of sensors, may detect (recognize) surrounding environment and objects, may generate map data, may determine the route and the travel plan, may determine the response to user interaction, or may determine the operation.

The robot 100a may use the sensor information acquired from at least one sensor among the lidar, the radar, and the camera so as to determine the travel route and the travel plan.

The robot 100a may perform the above-described operations by using the learning model composed of at least one artificial neural network. For example, the robot 100a may recognize the surrounding environment and the objects by using the learning model, and may determine the operation by using the recognized surrounding information or object information. The learning model may be learned directly from the robot 100a or may be learned from an external device such as the AI server 200.

At this time, the robot 100a may perform the operation by generating the result by directly using the learning model, but the sensor information may be transmitted to the external device such as the AI server 200 and the generated result may be received to perform the operation.

The robot 100a may use at least one of the map data, the object information detected from the sensor information, or the object information acquired from the external apparatus to determine the travel route and the travel plan, and may control the driving unit such that the robot 100a travels along the determined travel route and travel plan.

The map data may include object identification information about various objects arranged in the space in which the robot 100a moves. For example, the map data may include object identification information about fixed objects such as walls and doors and movable objects such as pollen and desks. The object identification information may include a name, a type, a distance, and a position.

In addition, the robot 100a may perform the operation or travel by controlling the driving unit based on the control/interaction of the user. At this time, the robot 100a may acquire the intention information of the interaction due to the user's operation or speech utterance, and may determine the response based on the acquired intention information, and may perform the operation.

The robot 100a, to which the AI technology and the self-driving technology are applied, may be implemented as a guide robot, a carrying robot, a cleaning robot, a wearable robot, an entertainment robot, a pet robot, an unmanned flying robot, or the like.

The robot 100a, to which the AI technology and the self-driving technology are applied, may refer to the robot itself having the self-driving function or the robot 100a interacting with the self-driving vehicle 100b.

The robot 100a having the self-driving function may collectively refer to a device that moves for itself along the given movement line without the user's control or moves for itself by determining the movement line by itself.

The robot 100a and the self-driving vehicle 100b having the self-driving function may use a common sensing method so as to determine at least one of the travel route or the travel plan. For example, the robot 100a and the self-driving vehicle 100b having the self-driving function may determine at least one of the travel route or the travel plan by using the information sensed through the lidar, the radar, and the camera.

The robot 100*a* that interacts with the self-driving vehicle 100*b* exists separately from the self-driving vehicle 100*b* and may perform operations interworking with the self-driving function of the self-driving vehicle 100*b* or interworking with the user who rides on the self-driving vehicle 100*b*.

At this time, the robot 100*a* interacting with the self-driving vehicle 100*b* may control or assist the self-driving function of the self-driving vehicle 100*b* by acquiring sensor information on behalf of the self-driving vehicle 100*b* and providing the sensor information to the self-driving vehicle 100*b*, or by acquiring sensor information, generating environment information or object information, and providing the information to the self-driving vehicle 100*b*.

Alternatively, the robot 100*a* interacting with the self-driving vehicle 100*b* may monitor the user boarding the self-driving vehicle 100*b*, or may control the function of the self-driving vehicle 100*b* through the interaction with the user. For example, when it is determined that the driver is in a drowsy state, the robot 100*a* may activate the self-driving function of the self-driving vehicle 100*b* or assist the control of the driving unit of the self-driving vehicle 100*b*. The function of the self-driving vehicle 100*b* controlled by the robot 100*a* may include not only the self-driving function but also the function provided by the navigation system or the audio system provided in the self-driving vehicle 100*b*.

Alternatively, the robot 100*a* that interacts with the self-driving vehicle 100*b* may provide information or assist the function to the self-driving vehicle 100*b* outside the self-driving vehicle 100*b*. For example, the robot 100*a* may provide traffic information including signal information and the like, such as a smart signal, to the self-driving vehicle 100*b*, and automatically connect an electric charger to a charging port by interacting with the self-driving vehicle 100*b* like an automatic electric charger of an electric vehicle.

Figure 4:
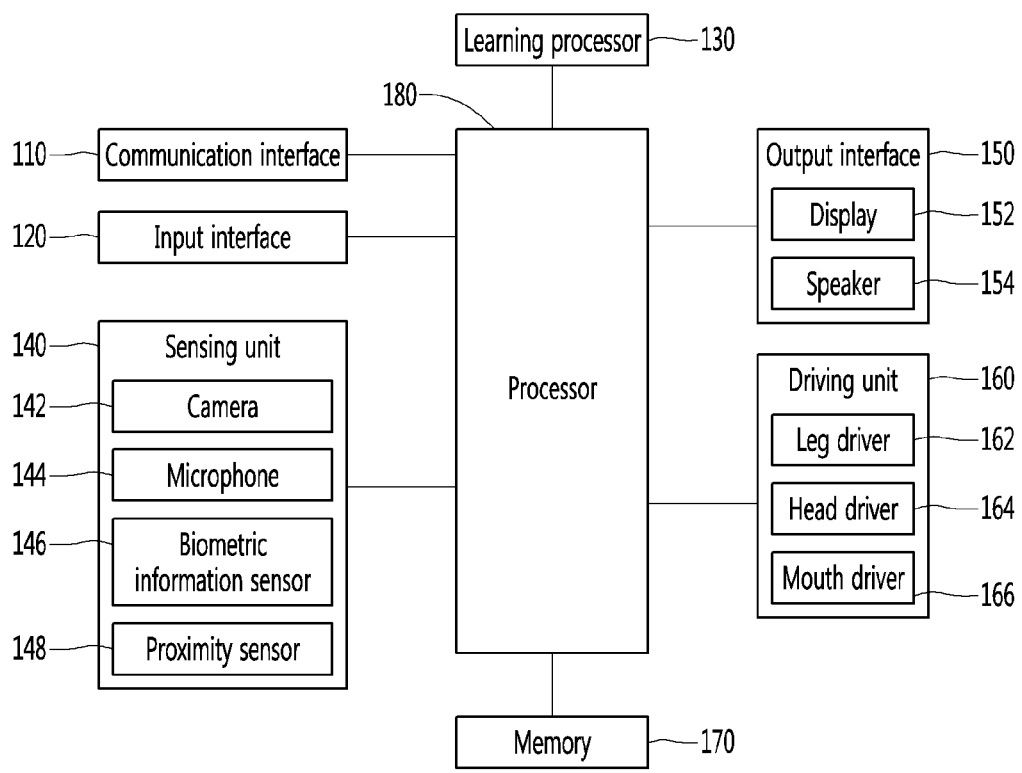
FIG. 4 is a block diagram illustrating a control configuration of a robot according to an embodiment of the present disclosure.

FIG. 4 is a block diagram illustrating a control configuration of a robot according to an embodiment of the present disclosure.

Referring to FIG. 4, the robot 100*a* may include a communication interface 110, an input interface 120, a learning processor 130, a sensing unit 140, an output interface 150, a driving unit 160, a memory 170, and a processor 180. Components illustrated in FIG. 4 is an example for convenience of description, and the robot 100*a* may include more or fewer components than those illustrated in FIG. 4.

Meanwhile, since the contents related to the AI device 100 of FIG. 1 are similarly applied to the robot 100*a* of the present disclosure, the contents overlapping with those described above with reference to FIG. 1 will be omitted.

The communication interface 110 may include communication modules for connecting the robot 100*a* to a server, a mobile terminal, another robot, or the like through a network. Each of the communication modules may support any one of the communication technologies described above with reference to FIG. 1.

For example, the robot 100*a* may be connected to a network through an access point such as a router. Accordingly, the robot 100*a* may provide various information acquired through the input interface 120, the sensing unit 140, or the like to a server or a mobile terminal through the network. In addition, the robot 100*a* may receive information, data, commands, and the like from the server or the mobile terminal.

The input interface 120 may include at least one input means for acquiring various types of data. For example, the at least one input means may include a physical input means such as a button and a dial, a touch input interface such as a touch pad or a touch panel, a microphone for receiving a voice of the user or a sound around the robot 100*a*, or the like. The user may input various requests or commands to the robot 100*a* through the input interface 120.

The sensing unit 140 may include at least one sensor which senses various information around the robot 100*a*.

For example, the sensing unit 140 may include a camera 142 for acquiring an image around the robot 100*a* and a microphone 144 for acquiring a voice around the robot 100*a*.

In addition, the sensing unit 140 may further include a biometric information sensor 146 for acquiring biometric information of the user.

The biometric information sensor 146 may include at least one sensor for acquiring a biometric signal related to various biometric information such as a heart rate, pulse characteristics (regularity, intensity, or the like), body temperature, stress, and oxygen saturation of the user. For example, the biometric information sensor 146 may include various types of sensors for acquiring a biometric signal based on photoplethysmography, or the like.

The processor 180 may acquire the biometric information from the biometric signal acquired through the biometric information sensor 146. In addition, the processor 180 may acquire health state information of the user based on the acquired biometric information. According to an embodiment, the processor 180 may transmit the acquired biometric information (or biometric signal) to the server through the communication interface 110 and acquire the health state information from the server.

According to an embodiment, the sensing unit 140 may further include a proximity sensor 148 which detects whether a part of a body of a user is in proximity. In the present embodiment, the biometric information sensor 146 is provided in a state of being hidden at a position of a part of the robot 100*a* and may be exposed to the outside as the proximity of a part of the body is detected by the proximity sensor 148.

An embodiment related to the disposition of the biometric information sensor 146 and the proximity sensor 148 will be described later with reference to FIGS. 5 to 6.

According to an embodiment, the sensing unit 140 may include various sensors such as an illumination sensor for detecting the brightness of the space in which the robot 100*a* is disposed and a gyro sensor for detecting the rotation angle or the inclination of the robot 100*a*.

The output interface 150 may output various information or contents related to the operation or the state of the robot 100*a*, various services, programs, applications, or the like, which are executed in the robot 100*a*. For example, the output interface 150 may include a display 152, a speaker 154, and the like.

The display 152 may output the various information, messages, or contents described above in graphic forms. According to an embodiment, the display 152 may be implemented as a touch screen together with a touch input interface.

The speaker 154 may output the various information, messages, or contents in the form of voice or sound.

The driving unit 160 may include at least one configuration related to the movement of the robot 100*a* and the motion (rotation, tilting, or the like) of certain parts of the robot 100*a*.

For example, the driving unit 160 may include a leg driver 162, a head driver 164, and a mouth driver 166. Each driving unit 162, 164, and 166 may include at least one motor for the movement or motion.

The driving unit 160 may include a moving portion having at least one motor for moving (driving or the like) the robot 100a. In the present specification, the leg driver 162 is illustrated as an example of the moving portion. However, in a case where the robot 100a includes another moving structure (wheel or the like) instead of the leg portion 102, the driving unit may include other types of moving portions other than the leg driver 162.

The leg driver 162 enables the movement of the robot 100a by providing a driving force for rotating at least one joint formed in the leg portion 102 (see FIG. 5) of the robot 100a.

The head driver 164 corresponds to a configuration for rotating or tilting the head portion 103 (see FIG. 5) of the robot 100a.

The mouth driver 166 corresponds to a configuration for opening and closing the mouth portion 104 of the robot 100a. As will be described later with reference to FIGS. 5 to 6, the mouth driver 166 rotates the rotatable portion (corresponding to a lower jaw) of the mouth portion 104 upward or downward, thereby enabling the opening and closing of the mouth portion 104.

A driving unit 160 is for moving (driving) the robot 100a and may include, for example, a driving motor. The driving motor may be connected to at least one wheel provided under the robot 100a to provide a driving force for driving the robot 100a to the at least one wheel. For example, the driving unit 160 may include at least one driving motor, and the processor 180 may adjust the driving direction and/or driving speed of the robot 100a by controlling the at least one driving motor.

Various data such as control data for controlling operations of components included in the robot 100a and data for performing operations based on input acquired through the input interface 120 or information acquired through the sensing unit 140 can be stored in the memory 170.

In addition, the memory 170 may store program data such as a software module and an application executed by at least one processor or controller included in the processor 180.

The memory 170 may include various storage devices such as a ROM, a RAM, an EPROM, a flash drive, a hard drive, and the like in hardware.

The processor 180 may include at least one processor, at least one controller, or the like which controls the operation of the robot 100a. In detail, the processor 180 may include at least one CPU, an application processor (AP), a microcomputer (or a micom), an integrated circuit, an application specific integrated circuit (ASIC), and the like.

Figure 5:
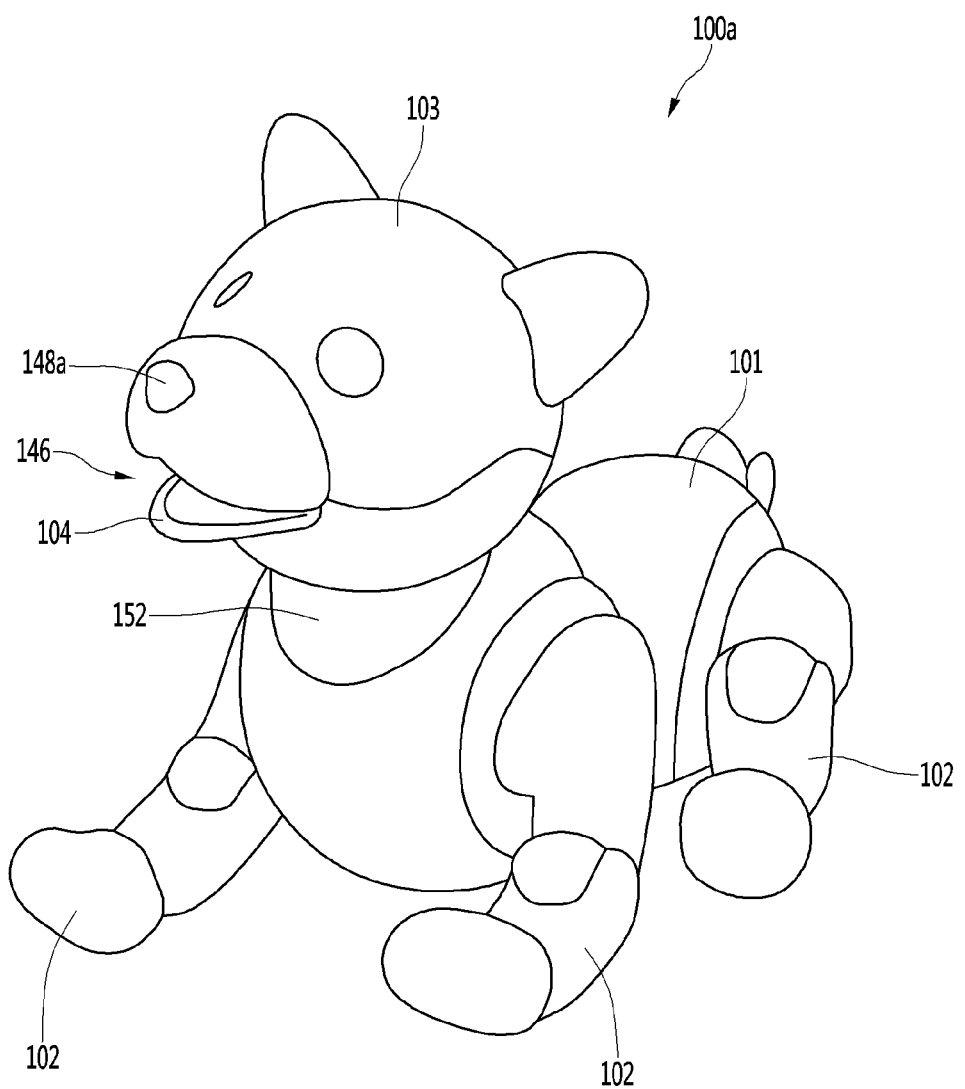
FIG. 5 is a perspective view illustrating a robot according to an embodiment of the present disclosure.
Figure 6:
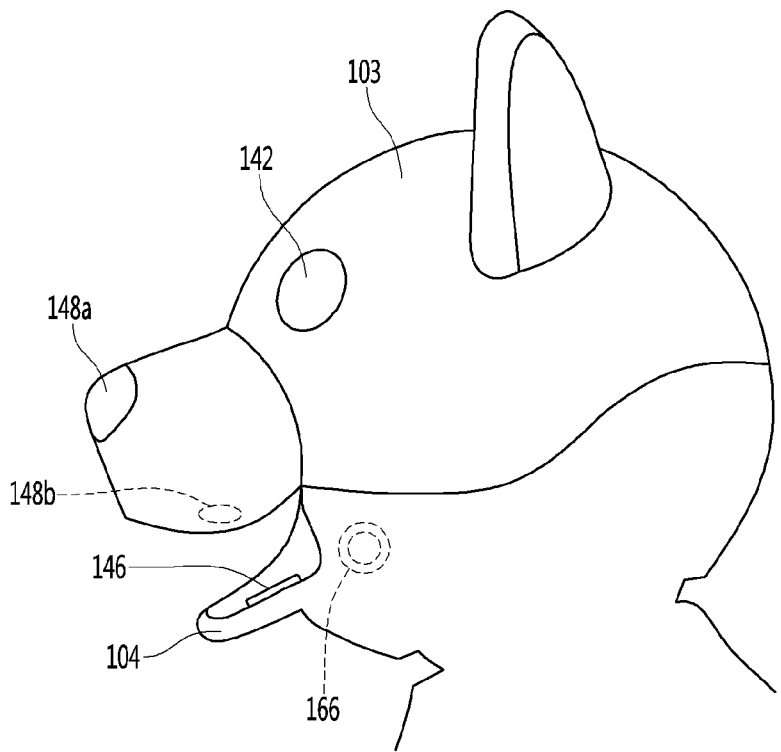
FIG. 6 is a view for explaining driving of a mouth of the robot illustrated in FIG. 5 and sensors provided in the mouth.

FIG. 5 is a perspective view illustrating a robot according to an embodiment of the present disclosure, and FIG. 6 is a view for explaining driving of a mouth of the robot illustrated in FIG. 5 and sensors provided in the mouth.

Referring to FIG. 5, the robot 100a according to an embodiment of the present disclosure may be implemented as a robot having a pet shape. Although the dog-shaped robot 100a is exemplarily illustrated in FIG. 5, the shape of the robot 100a is not limited thereto.

For example, the robot 100a may include a body portion 101, a leg portion 102, and a head portion 103, but the type or number of the component may be variously changed according to the shape of the robot 100a.

The body portion 101 may correspond to the body of the pet. For example, the body portion 101 may be provided with components for driving the robot 100a, for example, a PCB on which at least some of the control configurations illustrated in FIG. 4 are mounted, a battery for providing power, and the like. According to an embodiment, the display 152 may be implemented in the form of a neckband detachable to the body portion 101 of the robot 100a but is not necessarily so.

A leg portion 102 is a configuration corresponding to the leg of the pet and is connected to the body portion 101 to enable the movement of the robot 100a.

For example, leg portion 102 may include a plurality of legs, each of which may include a configuration corresponding to each of the legs, feet, and joints connected thereto. The leg driver 162 described above with reference to FIG. 4 includes at least one motor for rotating the configuration corresponding to the joint, and the robot 100a may move or motion according to the driving of the leg driver 162.

The head portion 103 is a configuration corresponding to the head of the pet and may be connected to the front or above the body portion 101. The head driver 164 described above with reference to FIG. 4 includes at least one motor for rotating, tilting the head portion 103, or the like, and the head portion 103 may move according to the driving of the head driver 164.

Meanwhile, the head portion 103 may include at least some of the components included in the sensing unit 140 such as a camera 142, a biometric information sensor 146, and a proximity sensor 148. For example, the camera 142 may be disposed at a position corresponding to the eye of the pet, but is not necessarily so.

Referring to FIGS. 5 to 6, a mouth portion 104 corresponding to the mouth of the pet may be formed at one side of the head portion 103. For example, the mouth portion 104 may include a fixed portion (for example, the upper jaw of the pet) formed in the head portion 103, and a rotatable portion (for example, the lower jaw of the pet) disposed below the fixed portion and rotatable in a vertical direction.

The mouth driver 166 may include a motor for opening and closing the mouth portion 104 (for example, rotation of the rotatable portion in the vertical direction). In detail, the mouth driver 166 may be provided inside the head portion 103 and may be connected to the rotatable portion of the mouth portion 104. As the mouth driver 166 is driven, the rotatable portion may rotate upward or downward. The mouth portion 104 may be closed in a case where the rotatable portion rotates upward, and the mouth portion 104 may be opened in a case where the rotatable portion rotates downward.

The biometric information sensor 146 may be provided inside the mouth portion 104. For example, the biometric information sensor 146 may be disposed at a position corresponding to the upper side of the rotatable portion or the tongue of the pet. Accordingly, since the biometric information sensor 146 may not be exposed to the outside in a state where the mouth portion 104 is closed, the risk of contamination or damage due to external factors may be minimized.

Meanwhile, the proximity sensor 148 may include a first proximity sensor 148a provided at a position corresponding to the nose of the robot 100a and a second proximity sensor 148b provided at the mouth portion 104. For example, the second proximity sensor 148b may be provided at a position corresponding to the lower side of the fixing portion of the mouth portion 104 or the palate of the pet. The proximity sensor 148 may be implemented as an optical sensor such as an infrared sensor to detect a distance to an object.

The first proximity sensor 148a may detect that a part of the body of the user is close to the mouth portion 104. For example, in a case where the health state monitoring function of the user is executed, the processor 180 may open the mouth portion 104 by driving the mouth driver 166 based on the detection result of the first proximity sensor 148a. As the mouth portion 104 is opened, a part of the body of the user (for example, a finger) may be in contact with the biometric information sensor 146.

When a part of the body is detected to be in contact with the biometric information sensor 146, the processor 180 may drive the mouth driver 166 to rotate the rotatable portion of the mouth portion 104 upward. The second proximity sensor 148b may detect that a part of the body of the user is close within a predetermined distance when the upper portion of the rotatable portion rotates. The processor 180 stops driving the mouth driver 166 based on the detection result of the second proximity sensor 148b, thereby fixing a part of the body of the user in the mouth portion 104 to be capable of acquiring an accurate biometric signal. This will be described in more detail later with reference to FIG. 8.

Figure 7:
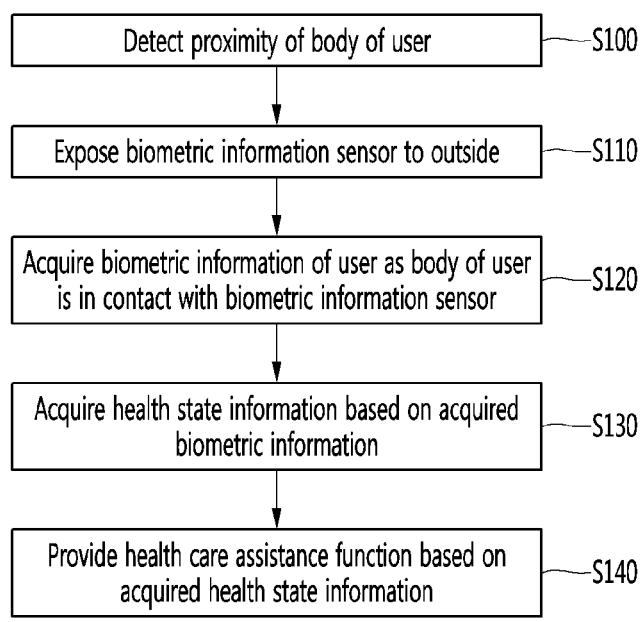
FIG. 7 is a flowchart for explaining a method for controlling a robot according to an embodiment of the present disclosure.

FIG. 7 is a flowchart for explaining a method for controlling a robot according to an embodiment of the present disclosure.

Referring to FIG. 7, the robot 100a may detect a proximity of a part of a body of a user (S100).

For example, the robot 100a may execute a health state monitoring function in response to a request received through the input interface 120 or the like.

As the health state monitoring function is executed, a user may be close to the robot 100a to contact a part of a body (for example, a finger) with the biometric information sensor 146.

The processor 180 may detect whether the part of the body of the user is close to the robot through the proximity sensor 148 (for example, the first proximity sensor 148a).

When the proximity of the part of the body of the user is detected, the robot 100a may expose the biometric information sensor 146 to the outside (S110).

When the proximity of the part of the body is detected through the first proximity sensor 148a, the processor 180 may control the driving unit 160 so as to expose the biometric information sensor 146 to the outside for the contact of the part of the body with the biometric information sensor 146.

As the body of the user contacts the biometric information sensor 146, the robot 100a may acquire biometric information of the user (S120).

As the biometric information sensor 146 is exposed to the outside, the user may contact the part of the body with the biometric information sensor 146.

As the body of the user contacts the biometric information sensor 146, the processor 180 may acquire a biometric signal related to the biometric information of the user through the biometric information sensor 146.

The processor 180 may acquire biometric information based on the acquired biometric signal. As described above, the biometric information may include a value (data) for each of at least one detailed information such as heart rate, pulse characteristics, body temperature, stress, and oxygen saturation.

The robot 100a may acquire health state information of the user based on the acquired biometric information (S130).

The processor 180 may acquire health state information of the user from the acquired biometric information.

For example, the processor 180 may acquire health state information corresponding to a value (data) of each of the detailed information included in the biometric information by using an algorithm related to the acquisition of the health state information.

According to an embodiment, the processor 180 may acquire the health state information through a learning model trained to provide health state information from each value of detailed information included in the biometric information. For example, the learning model may include an artificial neural network trained based on machine learning.

According to an embodiment, the processor 180 may control the communication interface 110 to transmit the acquired biometric information (or biometric signal) to the server. The server may generate health state information corresponding to the biometric information received from the robot 100a. The processor 180 may acquire the health state information by receiving the generated health state information from the server.

The robot 100a may provide a health care assistance function based on the acquired health state information (S140).

The processor 180 may control the components of the robot 100a to perform a function for health care of the user, based on the acquired health state information.

For example, the processor 180 may output a message for inducing an exercise of a user (jogging, walking, or the like) through the output interface 150 based on the health state information. The processor 180 controls the leg driver 162 to move the robot 100a for a preset distance or a preset time, thereby inducing a user to perform an exercise such as walking or running following the robot 100a. Meanwhile, the preset distance, time, exercise cycle, or the like may be changed and set based on the health state information of the user.

In addition, the processor 180 may provide various health care assistance functions such as accumulation and recording of a health care history including an exercise distance, an exercise time, or the like of the user and provision of a guide based on the recorded health care history.

Hereinafter, a case in which the embodiment of FIG. 7 is applied to the robot 100a having the exemplary structure illustrated in FIGS. 5 to 6 will be described in more detail with reference to FIGS. 8 to 13.

Figure 8:
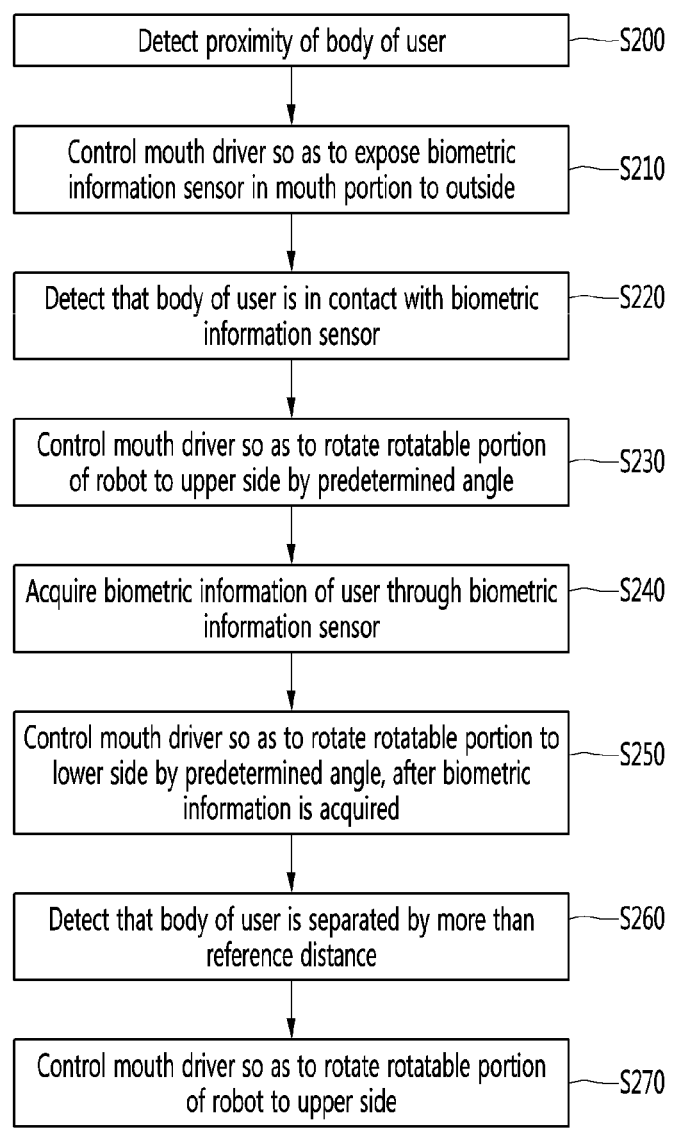
FIG. 8 is a flowchart for explaining an example of a specific control operation in which the robot according to an embodiment of the present disclosure acquires biometric information from the user.
Figure 9:
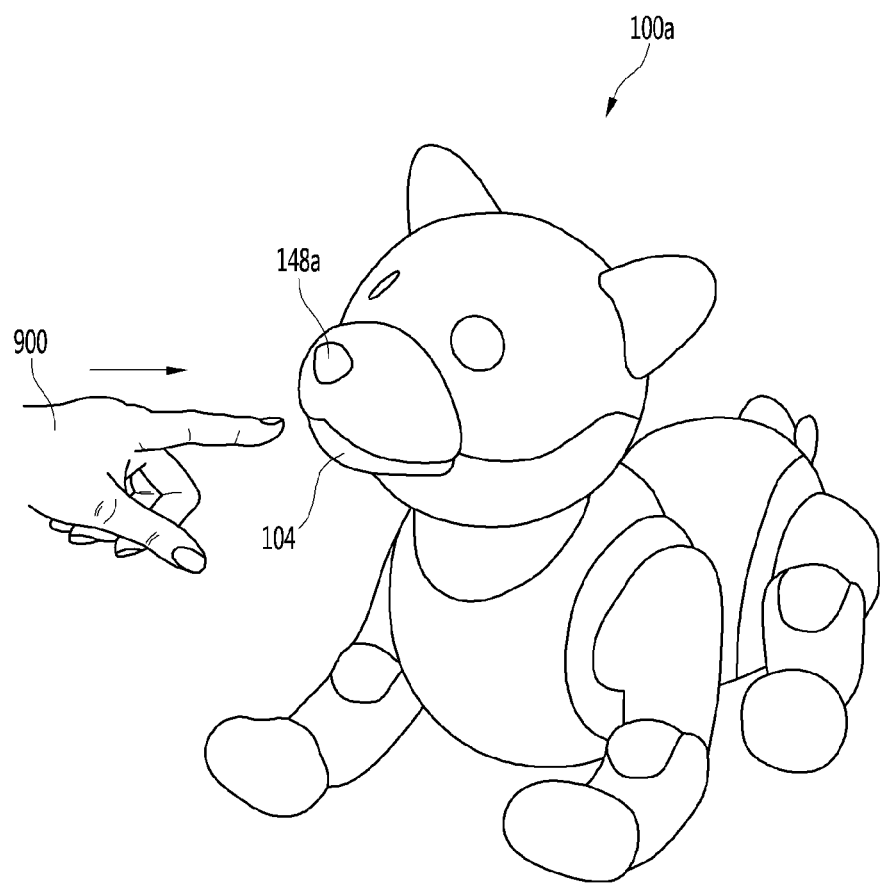
FIGS. 9 to 11 are exemplary views according to the control operation of the robot illustrated in FIG. 8.
Figure 10:
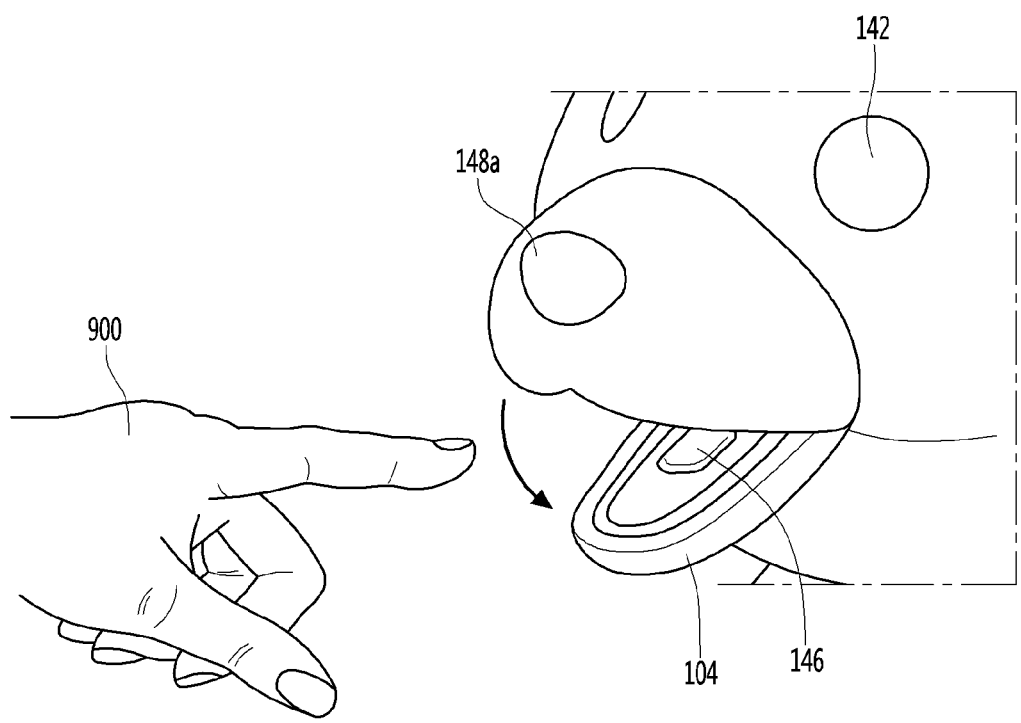
Figure 11:
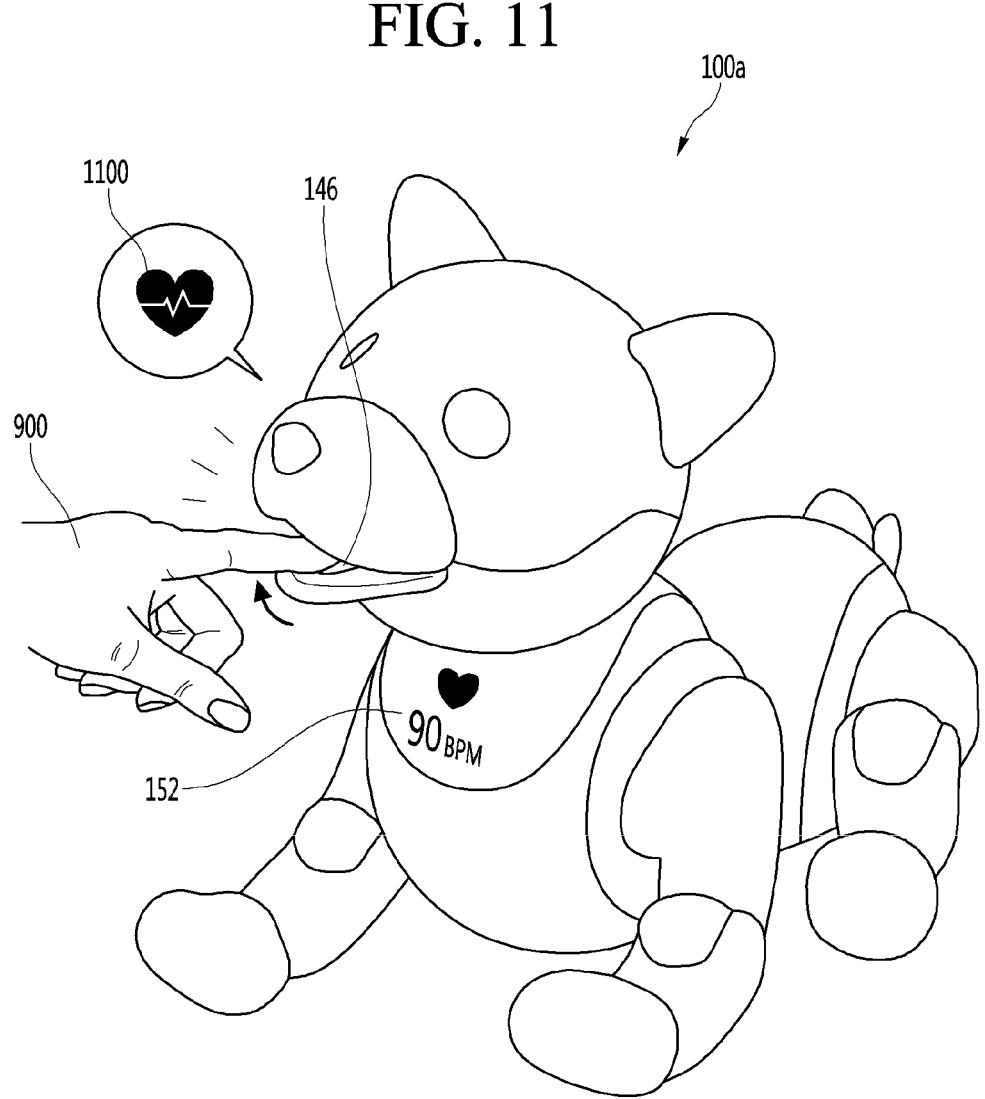

FIG. 8 is a flowchart for explaining an example of a specific control operation in which the robot according to an embodiment of the present disclosure acquires biometric information from the user. FIGS. 9 to 11 are exemplary views according to the control operation of the robot illustrated in FIG. 8.

Referring to FIG. 8, in a case where the proximity of a part of the body of the user is detected (S200), the robot 100a can control the mouth driver 166 so that the biometric information sensor 146 provided in the mouth portion 104 of the robot is exposed to the outside (S210).

As described above in step S100 of FIG. 7, the processor 180 may detect the proximity of the part of the body through the proximity sensor 148.

In this case, the processor 180 may control the mouth driver 166 to open the mouth portion 104. The mouth driver 166 may rotate the rotatable portion (corresponding to the lower jaw) of the mouth portion 104 downward by a predetermined angle to open the mouth portion 104.

As the mouth portion 104 is opened, the biometric information sensor 146 provided in the oral cavity may be exposed to the outside.

In this regard, referring to FIGS. 9 to 10, the processor 180 may detect the proximity of the finger 900 of the user through the proximity sensor 148. According to an embodiment, the processor 180 may detect that the finger 900 is close from the image acquired through the camera 142.

The processor 180 may control the mouth driver 166 so as to rotate the rotatable portion of the mouth portion 104 downward based on the detection result. As the rotatable portion rotates downward, the biometric information sensor 146 disposed on the upper surface of the rotatable portion may be exposed to the outside.

FIG. 8 will be described again.

The robot 100*a* can detect that the body of the user is in contact with the biometric information sensor 146 (S220), and control the mouth driver 166 so as to rotate the rotatable portion (lower jaw) of the mouth portion 104 upward by a predetermined angle (S230).

Referring to FIG. 11 together with FIG. 8, in a case where the mouth portion 104 is opened and the biometric information sensor 146 is exposed to the outside, the user inserts the portion of the body (for example, a finger 900) into the mouth portion 104 to contact the biometric information sensor 146.

The processor 180 may detect the contact of the body of the user through the biometric information sensor 146. According to an embodiment, the processor 180 may detect that the user' body is inserted into the mouth portion 104 so as to contact the biometric information sensor 146, through the second proximity sensor 148*b* (see FIG. 6) provided in the mouth portion 104.

When it is detected that the body of the user is in contact with the biometric information sensor 146, the processor 180 may control the mouth driver 166 so as to rotate the rotatable portion of the mouth portion 104 upward by a predetermined angle.

As the rotatable portion is rotated upward, the body (for example, finger 900) inserted into the mouth portion 104 may be stably fixed between the fixed portion and the rotatable portion of the mouth portion 104. Accordingly, since the movement of the body of the user in contact with the biometric information sensor 146 is minimized, more accurate biometric signal 1100 may be acquired by the biometric information sensor 146.

Meanwhile, in a case where the rotatable portion is continuously rotated upward, the user may feel pain as the body of the user is caught in the mouth portion 104. To prevent this, the processor 180 may stop the driving of the mouth driver 166 in a case where the sensing value acquired through the second proximity sensor 148*b* is less than the reference value during the upper rotation of the rotatable portion. Accordingly, the mouth portion 104 may maintain the open state by a predetermined angle based on the inserted body of the user.

FIG. 8 will be described again.

The robot 100*a* may acquire biometric information of the user through the biometric information sensor 146 (S240). After acquiring the biometric information, the robot 100*a* may control the mouth driver 166 to rotate the rotatable portion (lower jaw) downward by a predetermined angle (S250).

Referring to FIG. 11 together with FIG. 8, the processor 180 may receive the biometric signal 1100 for a predetermined time through the biometric information sensor 146 and acquire biometric information based on the received biometric signal 1100.

According to an embodiment, the processor 180 may output the acquired biometric information through the display 152.

The processor 180 may control the mouth driver 166 to rotate the rotatable portion downward by a predetermined angle after the biometric information (or biometric signal) is acquired. As the rotatable portion is rotated downward, fixing of the body in contact with the biometric information sensor 146 is released, and the body of the user may be moved out of the mouth portion 104.

FIG. 8 will be described again.

According to an embodiment, the robot 100*a* detects that a part of the body of the user is separated by a reference distance or more (S260) and controls the mouth driver 166 so as to rotate the rotatable portion (lower jaw) of the robot 100*a* upward (S260).

The processor 180 detects that a part of the body of the user is separated by the reference distance or more through the first proximity sensor 148*a* and/or the second proximity sensor 148*b* and rotates the rotatable portion upward to close the mouth portion 104. As the mouth portion 104 is closed, the biometric information sensor 146 may not be exposed to the outside.

Figure 12:
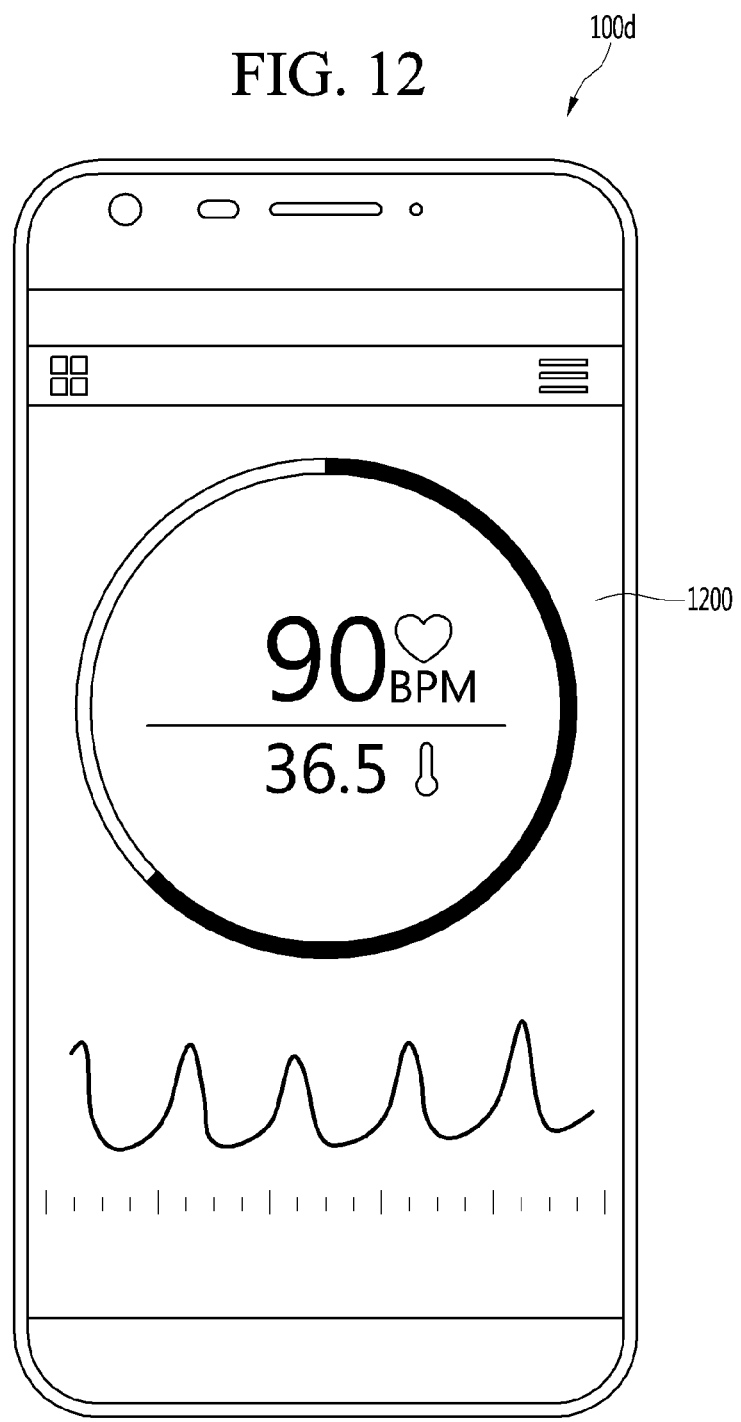
FIG. 12 is a view illustrating an example in which biometric information acquired by a robot is provided through a user terminal.

FIG. 12 is a view illustrating an example in which biometric information acquired by a robot is provided through a user terminal.

Referring to FIG. 12, the processor 180 of the robot 100*a* may transmit the acquired biometric information to the user terminal 100*d*. For example, the processor 180 may transmit the biometric information acquired in real time to the terminal 100*d*.

The processor of the terminal 100*d* displays a screen 1200 including the received biometric information on the display, thereby providing the biometric information to the user in real time.

According to an embodiment, the processor 180 may transmit the health state information acquired based on the biometric information to the terminal 100*d*.

Figure 13:
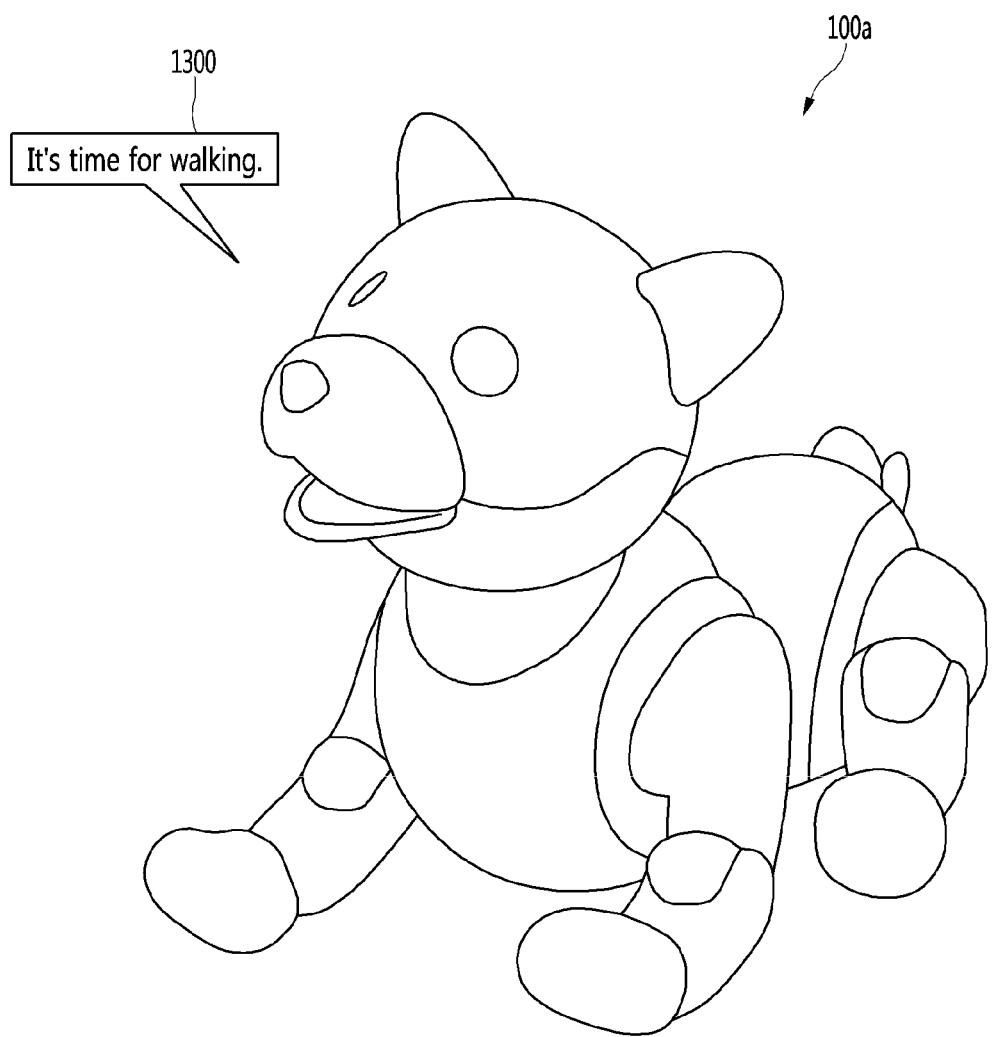
FIG. 13 is a view illustrating an example of an operation performed by the robot to assist health care of the user.

FIG. 13 is a view illustrating an example of an operation performed by the robot to assist health care of the user.

As described above in steps S130 to S140 of FIG. 7, the robot 100*a* may acquire health state information of the user based on the acquired biometric information. The processor 180 may provide an auxiliary function for health care of the user based on the acquired health state information.

As an example related to the auxiliary function, the robot 100*a* may perform a walking induction function for improving a health state of the user.

When an example of the walking induction function is described, the processor 180 may set at least one of a walking cycle, a walking time, and a walking distance based on the health state information of the user.

The processor 180 may output the walking guidance message 1300 through the speaker 154 or the like upon reaching the set walking cycle. The user may go out for a walk with the robot 100*a*, based on the output walking guidance message 1300.

When the processor 180 detects that the robot 100*a* is moved to the outside, the processor 180 may move the robot 100*a* by controlling the leg driver 162. The user may perform walking by walking or running following the moving robot 100*a*.

The processor 180 may assist the user in walking by moving the robot 100*a* based on the set time and/or the set distance.

The processor 180 may accumulatively generate and store an exercise history according to the execution of the walking assistance function, thereby acquiring information related to the health care of the user. The acquired information can be used later to check the health status of the user.

According to an embodiment of the present disclosure, the robot 100*a* can acquire the health state information of the user through the biometric information sensor 146 and provide various auxiliary functions for managing the health of the user based on the acquired health state information. In other words, the robot 100a may provide high utility by providing additional functions for health care, in addition to the emotional satisfaction provided by the pet.

In addition, the robot may minimize contamination or damage of the biometric information sensor by minimizing exposure to the outside when the biometric information sensor is not used. In addition, the robot effectively fixes the body of the user in contact with the biometric information sensor, thereby enabling the acquisition of accurate biometric information.

The above description is merely illustrative of the technical idea of the present disclosure, and those skilled in the art to which the present disclosure pertains may make various modifications and changes without departing from the essential characteristics of the present disclosure.

Therefore, the embodiments disclosed in the present disclosure are not intended to limit the technical idea of the present disclosure but to describe the technical idea of the present disclosure, and the scope of the technical idea of the present disclosure is not limited by these embodiments.

The protection scope of the present disclosure should be interpreted by the following claims, and all technical ideas within the scope equivalent thereto should be construed as being included in the scope of the present disclosure.

What is claimed is:

1. A robot comprising:
    a body which is provided with a battery therein;
    a head connected to a front or an upper side of the body;
    a mouth formed on one side of the head and including a fixed portion and a rotatable portion disposed below the fixed portion;
    a mouth driver configured to rotate the rotatable portion in a vertical direction;
    a biometric information sensor disposed inside the mouth and exposed to an outside during a lower rotation of the rotatable portion; a first proximity sensor provided in the head; and
    a processor configured to:
    control the mouth driver so as to rotate the rotatable portion downward by a predetermined angle in a case where proximity of a part of a body of a user is detected via the first proximity sensor,
    detect contact of the part of the body of the user via the biometric information sensor,
    control the mouth driver so as to rotate the rotatable portion upward, and
    acquire health state information of the user via the biometric information sensor.

2. The robot of claim 1 further comprising:
    a second proximity sensor provided on a lower side of the fixed portion,
    wherein the processor is configured to stop driving of the mouth driver in a case where a sensing value of the second proximity sensor is less than a reference value during an upper rotation of the rotatable portion.

3. The robot of claim 1,
    wherein the processor is configured to:
    acquire a biometric signal of the user for a preset time through via the biometric information sensor,
    acquire biometric information of the user based on the acquired biometric signal, and
    acquire the health state information based on the acquired biometric information.

4. The robot of claim 3,
    wherein the biometric information includes at least one of heart rate, pulse characteristics, body temperature, stress, and oxygen saturation.

5. The robot of claim 3,
    wherein the processor is configured to:
    acquire the health state information corresponding to the acquired biometric information through a learning model trained based on machine learning so as to provide the health state information from the biometric information.

6. The robot of claim 3 further comprising:
    a communication interface configured to connect to a server,
    wherein the processor is configured to:
    control the communication interface so as to transmit the biometric signal or the biometric information to the server, and
    receive the health state information corresponding to the biometric signal or the biometric information from the server.

7. The robot of claim 3,
    wherein the processor is configured to:
    control the mouth driver so as to rotate the rotatable portion downward after the biometric signal is acquired.

8. The robot of claim 7,
    wherein the processor is configured to:
    detect that the body of the user is separated by more than a reference distance via the first proximity sensor, and
    control the mouth driver so as to rotate the rotatable portion upward.

9. The robot of claim 1 further comprising:
    a second proximity sensor provided on a lower side of the fixed portion,
    wherein the processor is configured to:
    detect that the part of the body of the user is put into the mouth through via the second proximity sensor, and
    control the mouth driver so as to rotate the rotatable portion upward.

10. The robot of claim 1,
    wherein the processor is configured to:
    set at least one of a walking cycle, a walking time, and a walking distance based on the health state information,
    control an output interface so as to output a message for inducing walking based on the set walking cycle, and
    control at least one driving motor based on at least one of a set time and a set distance.

11. A method for controlling a robot, the method comprising:
    detecting proximity of a part of a body of a user via a first proximity sensor;
    controlling a mouth driver so as to rotate a rotatable portion of a mouth of the robot in which a biometric information sensor is provided to expose the biometric information sensor to an outside when the proximity is detected;
    acquiring biometric information of the user as the body of the user is in contact with the biometric information sensor;
    acquiring health state information based on the acquired biometric information; and
    providing a health care assistance function based on the acquired health state information.

12. The method for controlling a robot of claim 11,
wherein the acquiring the biometric information of the user includes:
　　detecting that the body of the user is in contact with the biometric information sensor; and
　　controlling the mouth driver so as to rotate the rotatable portion upward.

13. The method for controlling a robot of claim 12,
wherein the controlling the mouth driver so as to rotate the rotatable portion upward includes:
　　stopping driving of the mouth driver in a case where a sensing value acquired from a second proximity sensor included in the mouth is less than a reference value.

14. The method for controlling a robot of claim 12,
wherein the acquiring the biometric information further includes:
　　acquiring a biometric signal of the user for a preset time via the biometric information sensor; and
　　acquiring the biometric information based on the acquired biometric signal.

15. The method for controlling a robot of claim 14,
wherein the acquiring the biometric information further includes:
　　controlling the mouth driver so as to rotate the rotatable portion downward after the biometric signal is acquired.

16. The method for controlling a robot of claim 11,
wherein the providing the health care assistance function includes:
　　setting at least one of a walking cycle, a walking time, and a walking distance based on the health state information;
　　outputting a message for inducing walking based on the set walking cycle; and
　　controlling the robot so as to move based on at least one of a set time and a set distance.

17. The method for controlling a robot of claim 14,
wherein the biometric information includes at least one of heart rate, pulse characteristics, body temperature, stress, and oxygen saturation.

18. The method for controlling a robot of claim 15,
wherein the acquiring the biometric information further includes:
　　detecting that the body of the user is separated by more than a reference distance via the first proximity sensor; and
　　controlling the mouth driver so as to rotate the rotatable portion upward.

* * * * *